United States Patent [19]

Dechene et al.

[11] 4,288,741

[45] Sep. 8, 1981

[54] ELECTRICAL MEASUREMENT OF FLUID VOID FRACTION FOR FLUID HAVING CAPACITIVE AND RESISTIVE CONDUCTIVE COMPONENTS

[75] Inventors: Ronald L. Dechene, Boxford; Robert E. Newton, Tewksbury, both of Mass.

[73] Assignee: Auburn International, Inc., Danvers, Mass.

[21] Appl. No.: 40,326

[22] Filed: May 18, 1979

[51] Int. Cl.³ .......................................... G01R 27/26
[52] U.S. Cl. ................................................. 324/61 R
[58] Field of Search .................... 324/61 R, 434, 438; 73/61 R

[56] References Cited

U.S. PATENT DOCUMENTS

| | | | |
|---|---|---|---|
| 3,774,238 | 11/1973 | Hardway, Jr. | 324/61 R |
| 3,778,705 | 12/1973 | Maltby | 324/61 R |
| 4,174,498 | 11/1979 | Preikschat | 324/61 R X |
| 4,181,881 | 1/1980 | Preikschat | 324/61 R X |

*Primary Examiner*—Stanley T. Krawczewicz
*Attorney, Agent, or Firm*—Jerry Cohen

[57] ABSTRACT

Liquid with solid or gas phases mixed therein is measured as to liquid and non-liquid volume percent by application of an oscillating voltage to the liquid and separation of resultant conductive and capacitive currents to achieve valid and effective measurement of the latter, unmasked by the larger conductive currents obtainable in the mixed phase medium analyzed.

4 Claims, 5 Drawing Figures

ELECTRICAL MEASUREMENT OF FLUID VOID FRACTION FOR FLUID HAVING CAPACITIVE AND RESISTIVE CONDUCTIVE COMPONENTS

BACKGROUND OF THE INVENTION

Prior U.S. Pat. Nos. 4,074,184 granted 2/14/78, 4,063,153 granted 12/13/77 and 4,082,994 granted 4/4/78, all of common assignment with the application describe inventions for measuring respective fractions of mixed phased fluids, particularly gas and conductive liquid or solids entrained in liquids utilizing means particularly suited for flow which develops a conductance under a voltage field or alternatively utilizing capacitance techniques for non-conductive fluids.

However, there remains a need for means for measuring liquid content of a mixed stream of liquid and gas in situtations when the liquid fraction of a stream may be very samll (less than 10%)—a condition occurring, for instance, in some steam flows, which may be measured.

It is therefore the object of the invention to provide commercially practical apparatus meeting such need reliably and economically.

SUMMARY OF THE INVENTION

In accordance with the present invention, the amount of liquid is measured by employing its dielectric characteristics. There are two distinct advantages of employing a dielectric capacitive measurement of the amount of water present as a means of establishing respective fractions of water and gas. First, the water does not have to form a conductive lattice between electrodes as is required in conductive or impedance techniques. Second, the dielectric constant of water is very high when compared with most other materials. When the direct measurement of the capacitive component of water is attempted, the rather large conductive component usually causes amplifier overload. The practice of the present invention involves means to automatically cancel out the conductive component to prevent amplifier overloading.

Other objects, features and advantages of the invention will be apparent from the following detailed description of preferred embodiments thereof, taken in connection with the accompanying drawing, in which:

BRIEF DESCRIPTION OF THE DRAWING

FIGS. 1A–1C are voltage vs. time traces taken for different points of the circuit of FIG. 1, as mentioned below.

DETAILED DESCRIPTION OF PREFERRED EMBODIMENTS

Figure 1:
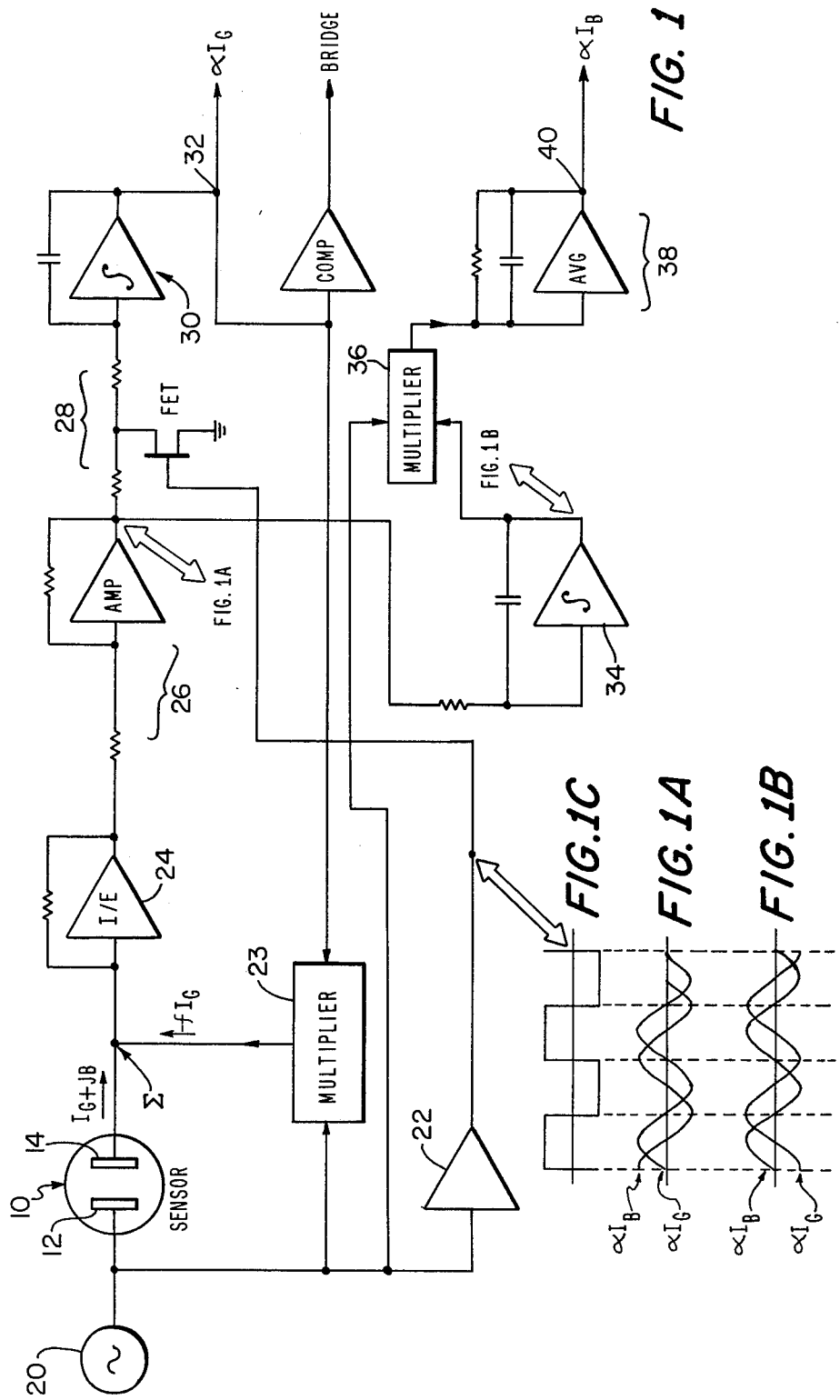
FIG. 1 is a block diagram of a circuit to accomplish the automatic cancellation of the conductive components.

The FIG. 1 circuit comprises a sinusoidal oscillator 20 which drives one plate, e.g., 12 of a sensor 10 so that a current ($I_G+jB$), due to both the conductive and capacitive components, appears at the opposed plate 14. The sensor 10 and electrical circuit components, unless stated otherwise herein, can be essentially described in the above cited U.S. patents, which are incorporated herein by reference as though set out at length herein.

The oscillator output also is fed to a comparator 22 to detect the axis crossing of the sensor excitation voltage (See FIG. 1C). Also, the oscillator is fed to one input of multipliers 23 and 36. The current from the sensor plate enters the summing junction ($\Sigma$) input of an amplifier 24 which translates the current to a voltage signal with some effective gain. A second voltage gain stage indicated at 26 further amplifies the signal. A FET switch circuit 28, driven by the comparator 22, (See FIG. 1A) commutates the said amplified voltage signal in synchronism with the oscillator into an integration circuit 30 (rectification is also achieved). The output of the averaging circuit taken off at point 32 of the circuit is proportional to the conductive current $I_G$ (in phase component) of the sensor current. The signal from the amplifier 26 is also fed to an integrator 34 which shifts the phase of the signal by 90°; therefore, the capacitive (quadrature) current signal is shifted into phase with the output of the oscillator See FIG. 1B).

The output of the integrator enters multiplier circuit 36 which feeds an averager 38. The output of the averager 38 taken at point 40 is a signal proportional to the capacitive current $I_B$ (quadrature current) of the sensor. Since the conductive current of the sensor usually far exceeds (in water) the capacitive current, the amplifiers would be driven into saturation unless some means of nulling the conductive current is employed. To accomplish this, the proportional conductive component output of signal available at 32 is fed back to the second input of the multiplier 23. The output of the multiplier is an inversion of the oscillator input to the multiplier, but varying in amplitude. The output of the multiplier is a current, and as such is fed directly into the summing junction ($\Sigma$) as a signal nearly nulling the conductive component of the sensor current. The averaged output (at 32) is now an error signal proportional to the conductive component $I_G$. The signal levels in the amplifiers are now reduced to non-saturation levels. Thus, it is possible to measure a relatively small value of capacitance in the presence of a rather large conductance.

After considerable experimentation, it became evident that unless the plates were bridged by water, the field would tend to locate in the gap, thus reducing the apparent capacitive output due to the presence of the water. A logical output derived from the conductive output would allow an operator to provide further gain at the capacitive output.

Figure 2:
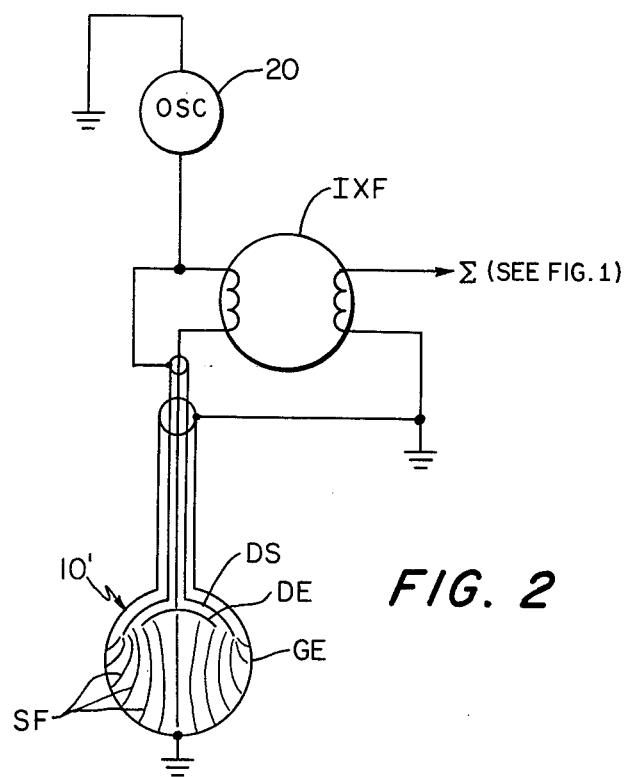
FIG. 2 is a schematic of a variant embodiment of the invention.

A further refinement is to drive the sensor input to ground, eliminating one active plate, as shown in FIG. 2 where a current transformer IXF extracts a measured current from a grounded sensing electrode GE for application to the summing junction $\Sigma$. Also, a driven shield DS is extended to form an electrode around the driven electrode DE to focus the sensing field SF.

It is evident that those skilled in the art, once given the benefit of the foregoing disclosure, may now make numerous other uses and modifications of, and departures from the specific embodiments described herein without departing from the inventive concepts. Consequently, the invention is to be construed as embracing each and every novel feature and novel combination of features present in, or possessed by, the apparatus and techniques herein disclosed and limited solely by the scope and spirit of the appended claims.

What is claimed is:

1. Method of measuring a liquid content of mixed phase fluid in a container wherein a conductive liquid contains voids therein comprising, making a capacitive current measurement between two spaced (in cross-section of the fluid container) electrodes, and cancelling out a conductive (electrically) component of the current measurement through the fluid inherently picked up in making the capacitive measurement so that the capacitive measurement is not masked by the conductive measurement and wherein the measured current is produced by application of an oscillating voltage to the electrodes and the output capacitive current component (or a voltage derivative thereof) is shifted into phase with the oscillating voltage.

2. Method in accordance with claim 1 wherein the conductive current component is attenuated, through feedback, and amplified, without saturation of amplifier apparatus.

3. Apparatus for practice of the method of either of claims 1 or 2 comprising, means for applying an oscillating voltage to a mixed phase medium including relatively conductive liquid and relatively non-conductive second phase, first means for detecting current produced by said voltage in the medium as a current signal with mixed and varying conductive and capacitive components, second means applying such current to a summing junction together with a valid transfer function derivative of the conductive component, third means for producing such valid transfer function, fourth means for converting a current output of the summing junction to a voltage and applying components thereof to separate means for indicating conductive and capacitive components of the original measured component.

4. Apparatus in accordance with claim 3 wherein said third means include a feedback loop with voltage derivative of conductive component of current applied together with the oscillating voltage to a multiplier which produces a current output as a negative sign transfer function of conductive component of measured current.

* * * * *